(12) United States Patent
Rocher

(10) Patent No.: US 6,616,449 B1
(45) Date of Patent: Sep. 9, 2003

(54) ARTICULATOR FOR PRODUCING DENTAL PROSTHESES

(76) Inventor: Pascal Rocher, 108 Avenue Gustave Eiffel, 21000 Dijon (FR)

( * ) Notice: Subject to any disclaimer, the term of this patent is extended or adjusted under 35 U.S.C. 154(b) by 0 days.

(21) Appl. No.: 09/721,095

(22) Filed: Nov. 22, 2000

Related U.S. Application Data

(63) Continuation of application No. PCT/FR99/01197, filed on May 20, 1999.

(30) Foreign Application Priority Data

May 25, 1998 (FR) .............................................. 98 06521

(51) Int. Cl.[7] .............................................. A61C 11/00
(52) U.S. Cl. .......................................... 433/55; 433/56
(58) Field of Search .............................. 433/55, 56, 57, 433/58, 59, 60, 61, 62, 63, 64, 65, 66, 67, 68, 69, 70, 71, 72, 73

(56) References Cited

U.S. PATENT DOCUMENTS

| | | | | |
|---|---|---|---|---|
| 1,498,559 A | * | 6/1924 | Lightcap | 433/56 |
| 3,409,986 A | * | 11/1968 | Freeman | 433/55 |
| 4,504,226 A | * | 3/1985 | Gordon | 433/63 |
| 5,281,135 A | * | 1/1994 | Schwestka-Polly | 433/56 |
| 5,738,515 A | * | 4/1998 | Leever | 433/55 |
| 6,109,917 A | * | 8/2000 | Lee et al. | 433/73 |

FOREIGN PATENT DOCUMENTS

| | | |
|---|---|---|
| DE | 38 13956 A1 | 11/1989 |
| DE | 42 11 017 A1 | 10/1993 |
| DE | 196 21 800 A1 | 12/1997 |

* cited by examiner

*Primary Examiner*—John J. Wilson
(74) *Attorney, Agent, or Firm*—Heslin Rothenberg Farley & Mesiti P.C.; Victor A. Cardona, Esq.

(57) ABSTRACT

The invention concerns an articulator for parametering a prosthetic or occlusal directional plane and dentoalveolar stages, for producing dental prostheses. The device includes two planar elements, upper and lower (1, 2), mutually articulated about a horizontal pin (3) parallel to the two planar elements (1, 2) and located above the lower planar element (2). The two planar elements are designed to fix, opposite each other and in contact with each other, a patient's two dental arch models (5, 6), namely an upper model (5) fixed beneath the upper element (1) lower surface and a lower model (6) fixed on the lower element (2) upper surface, and means for defining, between the two elements (1, 2) a plane inclined with respect to the upper element (1) and corresponding to an occlusal plane P between the two models (5, 6). The means defining the inclined plane corresponding to the occlusal plane P are borne by the upper element (1). They include a plate (7) representing the occlusal directional plane P. They are means for adjusting (8, 9; 13; 56–59; 64–70) the angle of inclination and the distance between the plate (7) and the upper element (1). The distance between the plate (7) and the upper element (1) is adjusted by an assembly (9) borne by the upper element (1) and a column provided with a scale (8) bearing the plate (7) at its lower end and sliding perpendicularly to the upper element (1) in the assembly (9), guiding the column (8) and locking into a position adjustable relative to the upper element (1).

21 Claims, 10 Drawing Sheets

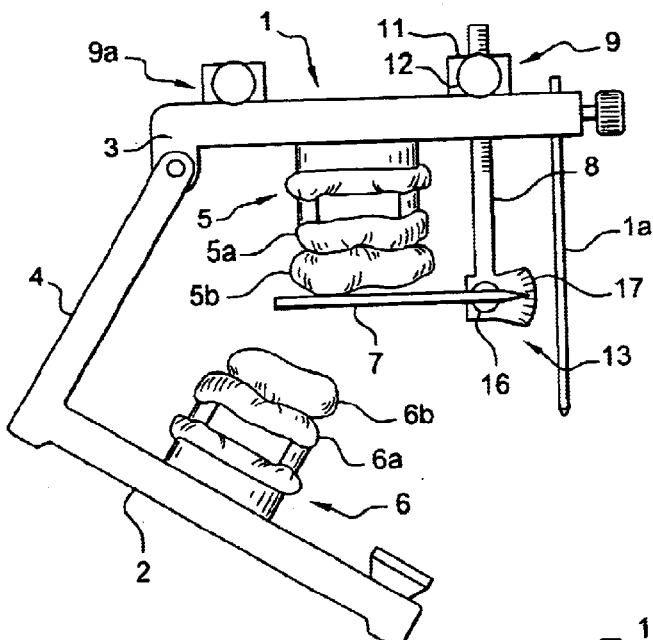
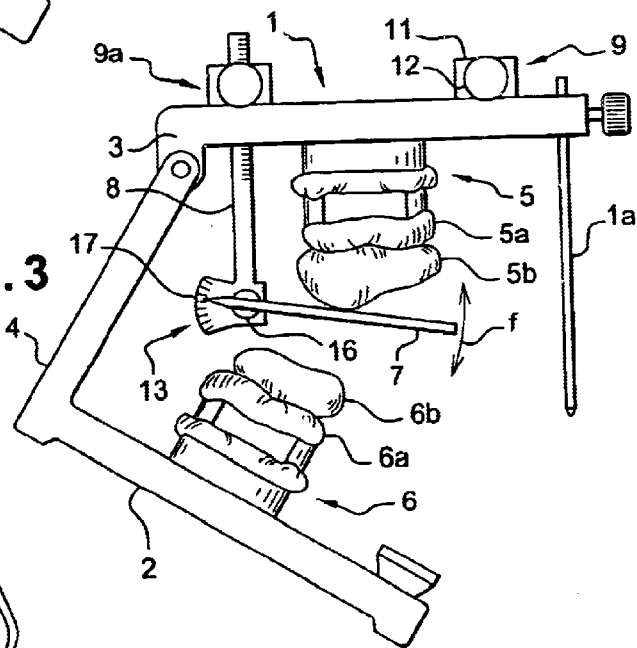
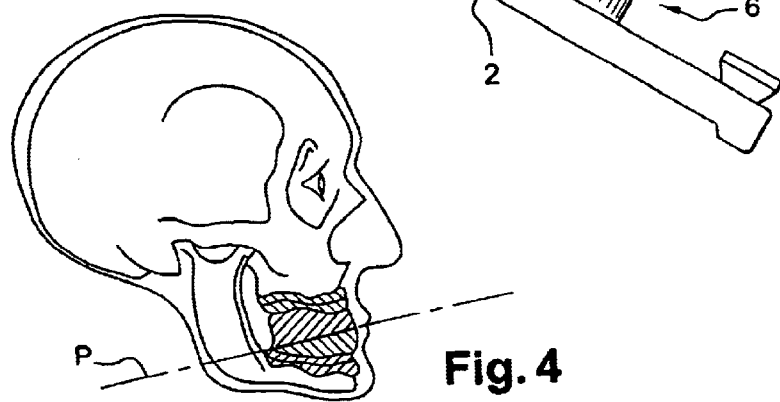

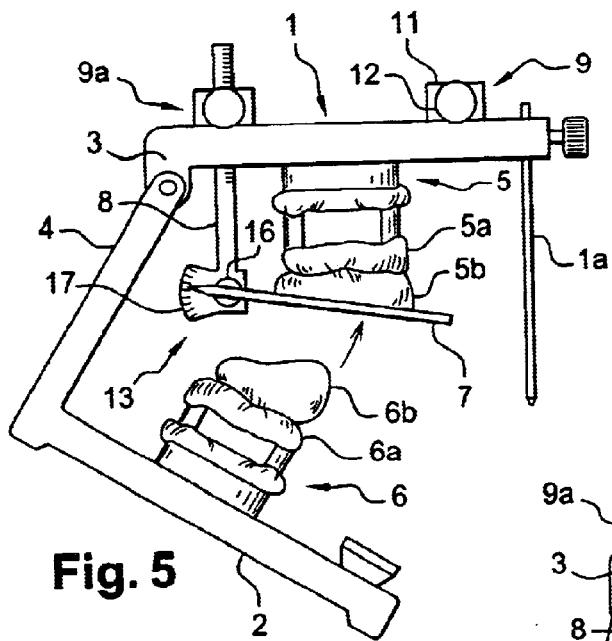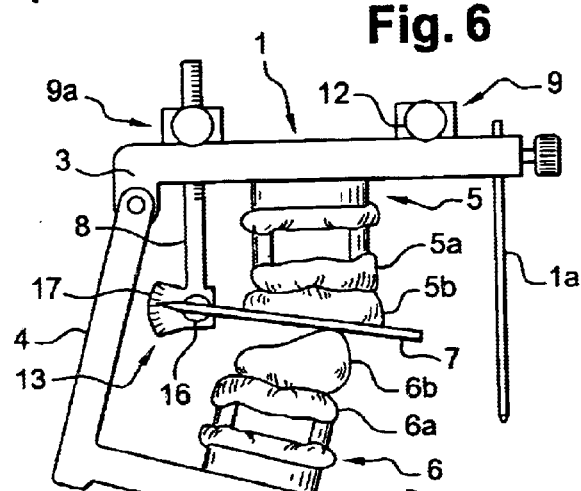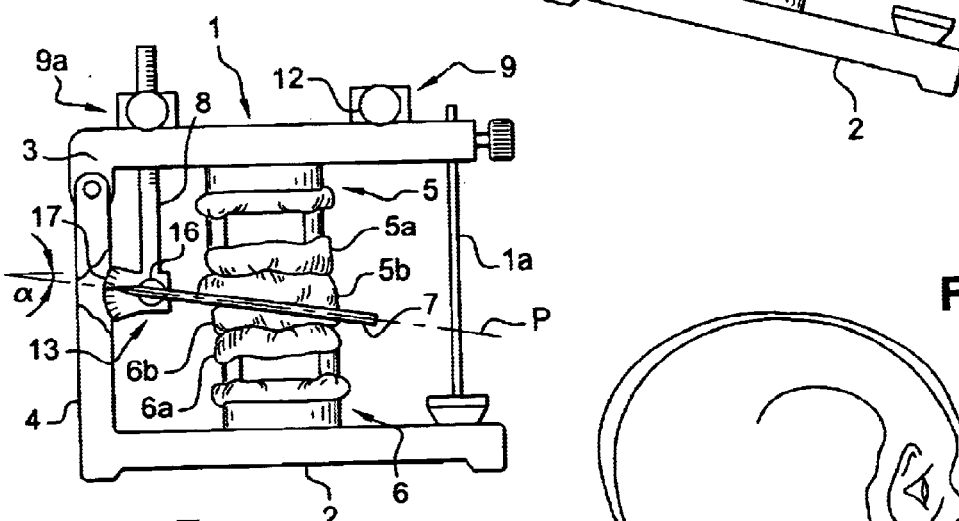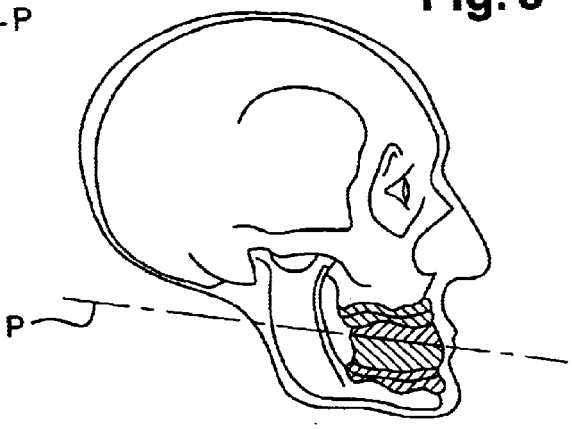

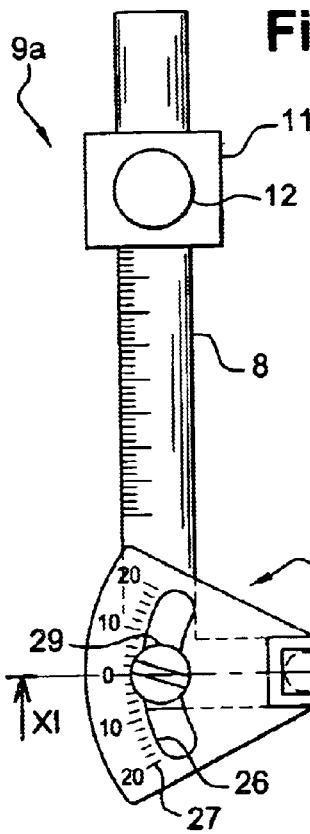
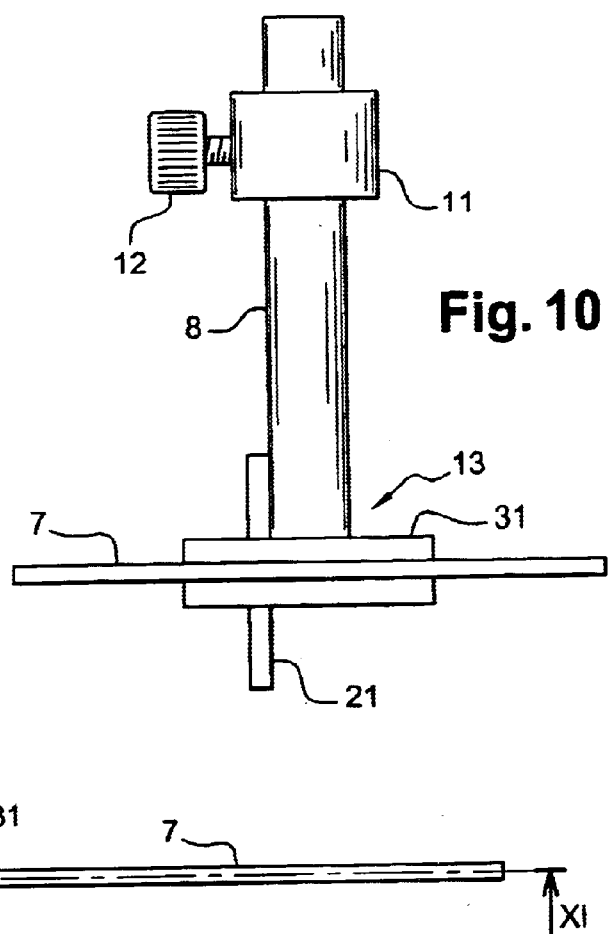
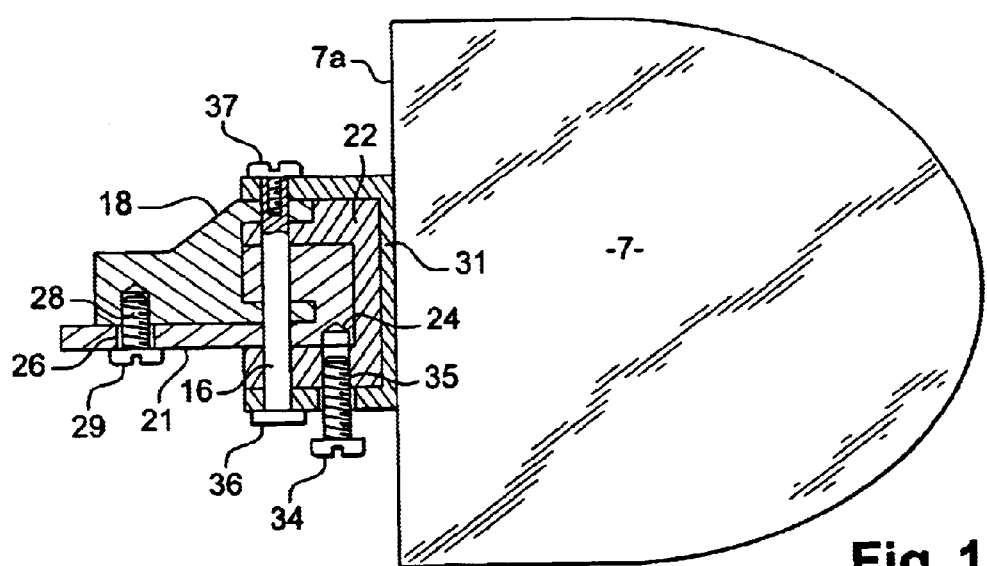

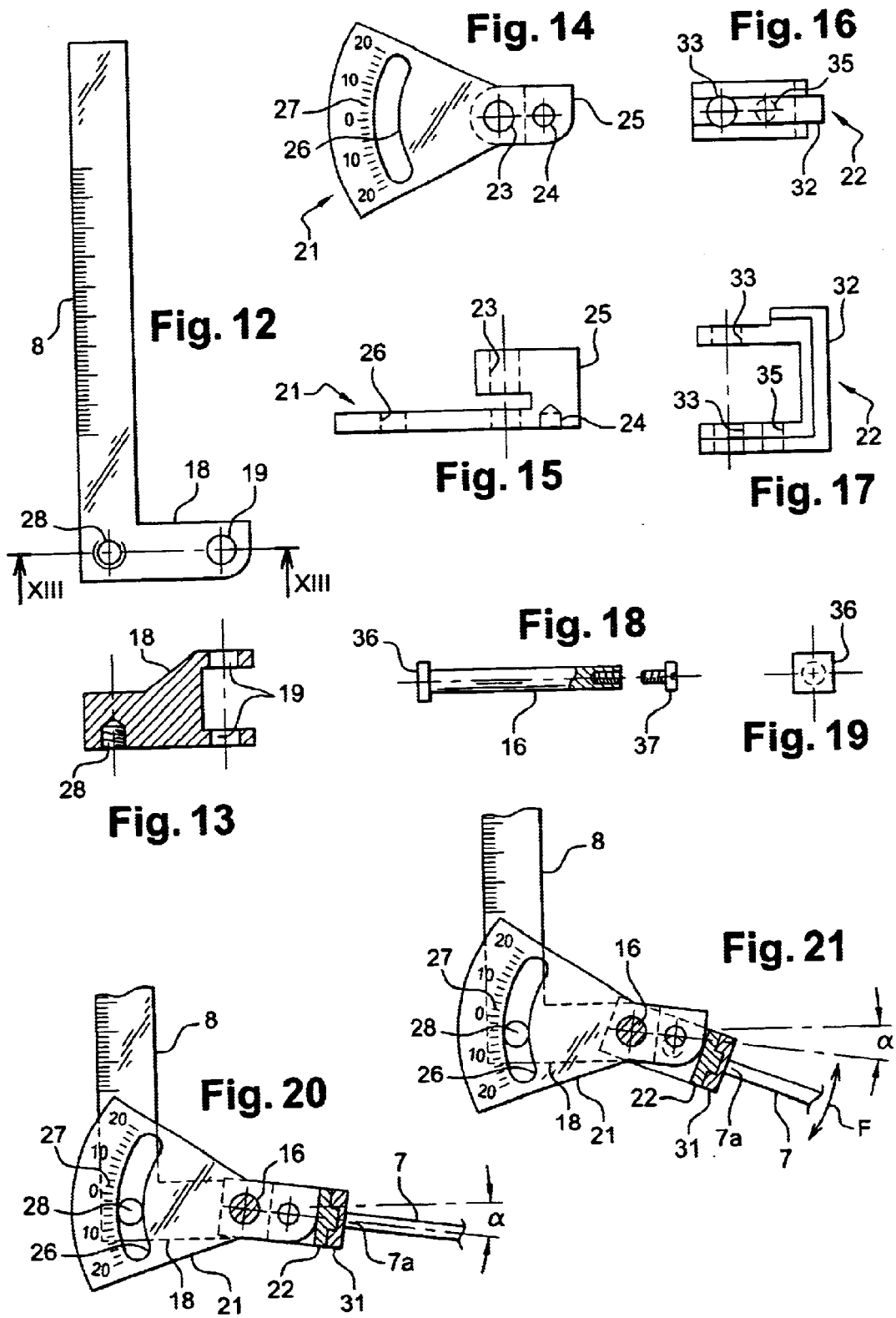

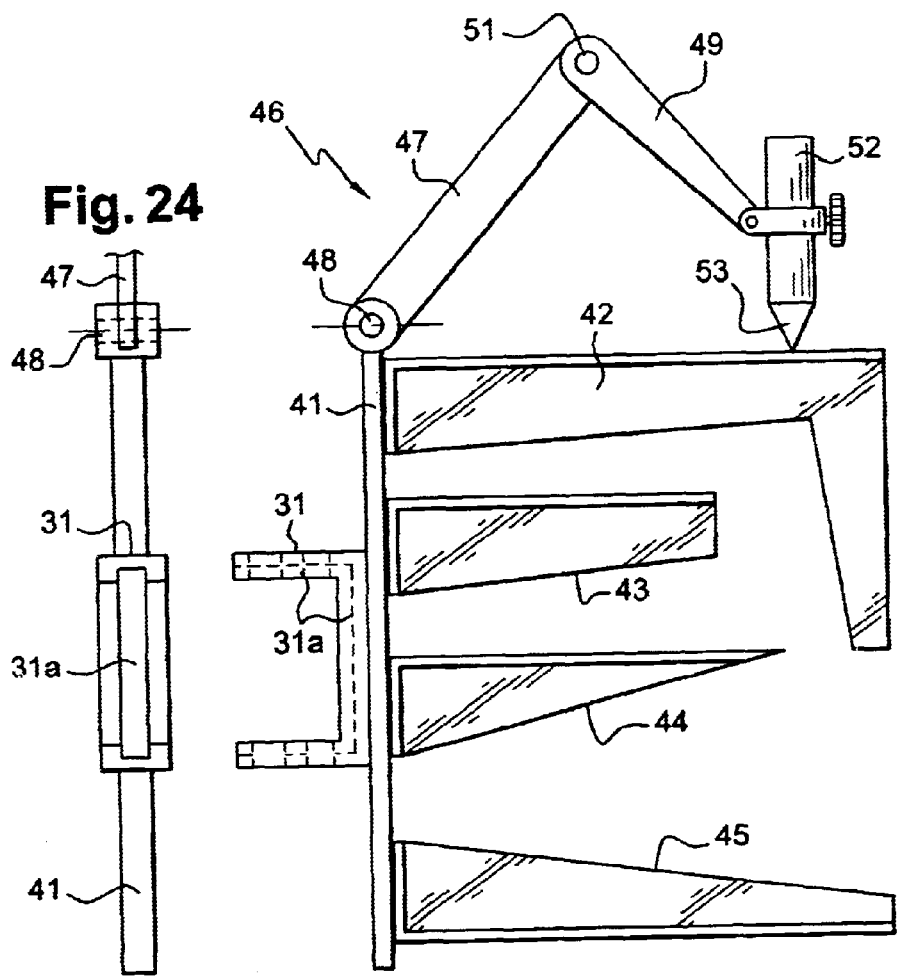
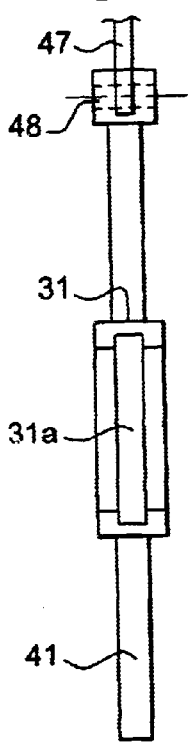
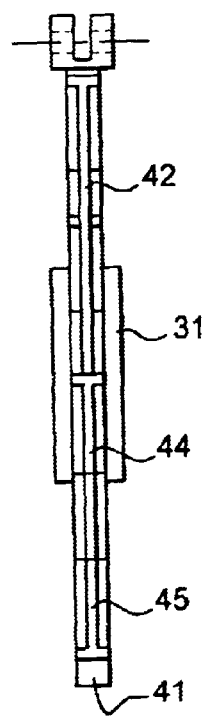
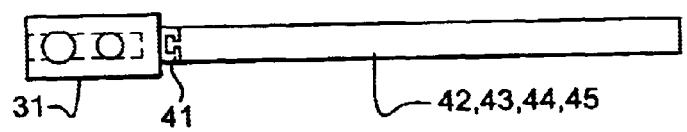
Fig. 22
Fig. 24
Fig. 25
Fig. 23

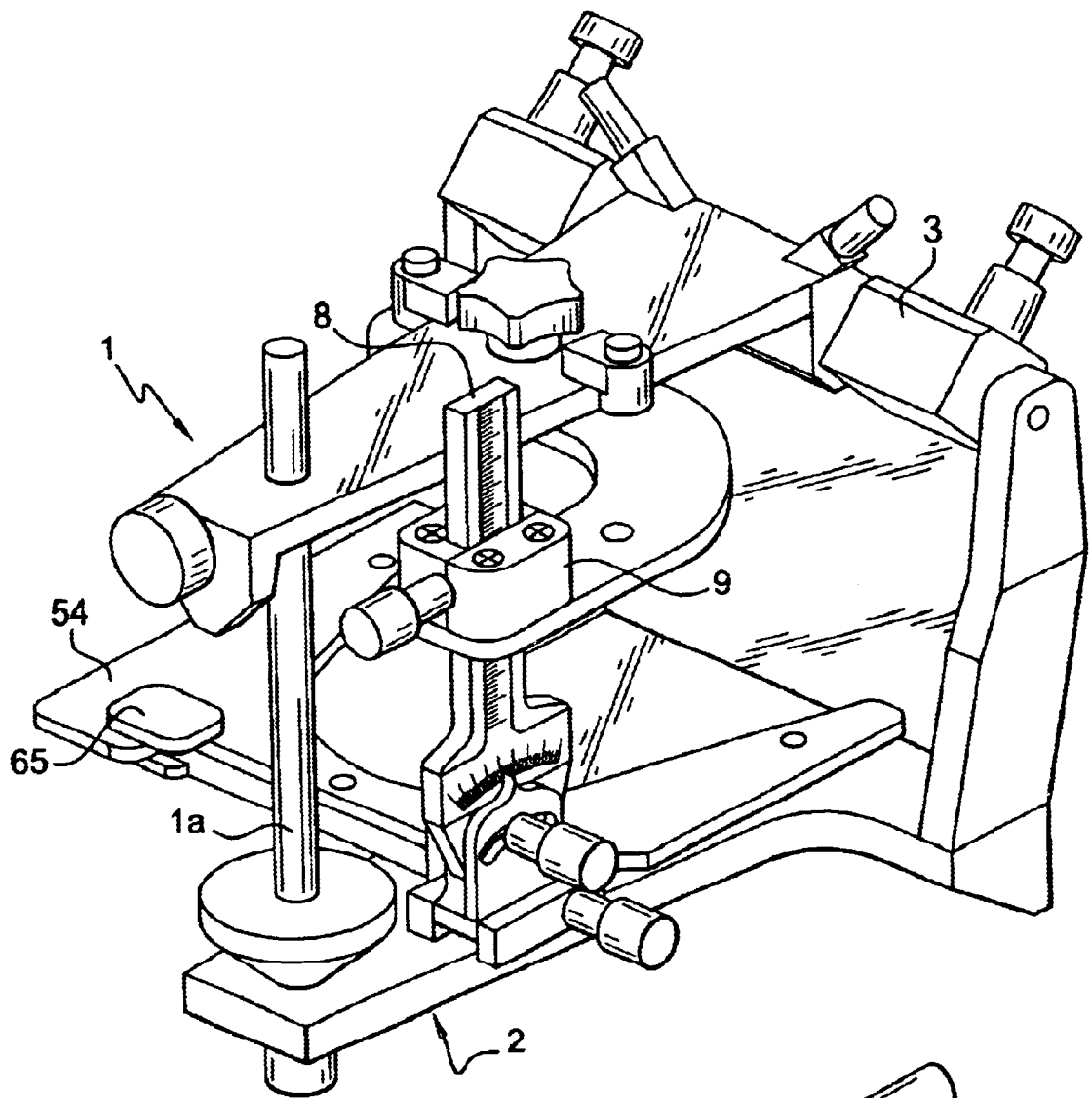
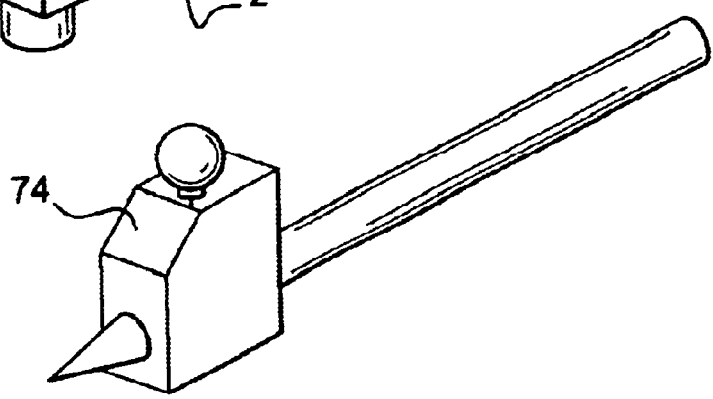
Fig. 31

ARTICULATOR FOR PRODUCING DENTAL PROSTHESES

The present invention relates to an articulator making it possible to parametrize the prosthetic or occlusal orientation plane and the dentoalveolar stages for the purpose of producing dental prostheses.

For the production of dental prostheses, use is made at the present time of articulators of the "ARCON" type, employed most often, or else "NONARCON" type. These appliances, used in dental prosthesis laboratories and in dental surgeries, serve for reproducing the envelope of natural physiological movements between the dental arches of a patient in relation to his skull, for the purpose of manufacturing bridges, prostheses, etc. in a laboratory.

These appliances generally comprise two planar elements or members, respectively lower and upper, which are articulated relative to one another about a horizontal axis parallel to the plane of the two elements and located at a level higher than that of the lower planar element. Plaster models of a patient's dental arches are fastened to these upper and lower planar elements which reproduce as it were the patient's jaws. These models comprise an upper model, reproducing the upper dental arch and fastened under the lower face of the upper element, and a lower model, reproducing the lower dental arch and fastened to the upper face of the lower element. When the number of antagonistic teeth allows it, there is natural wedging between the middle stage of the face and the lower stage of the face. This preserves the vertical occlusal dimension which is conducive to the esthetic appearance of the face. This vertical dimension is therefore transferred to the articulator, when the plaster models of the patient's dental arches are mounted, by means of the facial arch and in occlusion. On the articulator, the two models of the patient are fastened opposite one another, so as to come into contact with one another along an occlusal plane which corresponds to the occlusal plane of the patient's dental arches. Cephalometry is the study of the craniofacial structures on X-ray photographs of the head, profile or face. It is possible, on a profile teleradiogram, to trace the horizontal Frankfurt plane, which passes through the top of the image of the right and left external auditory meatuses and the images of the infraorbital foramens, and also the patient's occlusal plane defined as the occlusal plane traced by recording the intermeshing zone of the first molars and central incisors. In a patient with normodivergent teeth, the occlusal plane is the plane of contact between the top teeth and the bottom teeth, and it is generally inclined from the top downward and from the rear forward at an angle of 10° in relation to the horizontal Frankfurt plane.

There are on the market accessories which make it possible to parametrize the occlusal plane, but these accessories do not make it possible to parametrize as easily between the two mounted dental arch models; nor do they make it possible to manufacture in a laboratory occlusal mock-ups or temporary bridges which conform to the parametrization defined by the practitioner's study. Nor is it possible for these accessories to make it possible to trace the prosthetic orientation plane on the plaster models of the patient's dental arches.

In the articulators known at the present time, the upper plaster model mounted on a plate fastened to the lower element of the articulator, at a predetermined height above this element and inclined at an angle of 10° from the top downward and from the rear forward in relation to the upper element, is useful only for a normodivergent patient whose upper arch occupies spatially the position in relation to the skull which this standard plate imposes on it. In fact, such a fixed height and such a fixed inclination do not correspond to the generality of cases encountered in practice in the various patients treated, who have a craniofacial scheme which may range from hypodivergence to hyperdivergence. In such circumstances, mounting the maxillary model of the patient's dental arch along this standard plane is tantamount to neglecting the spatial position of the maxillary arch in relation to the base of the skull. In other words, a standard plane of a typical normodivergent patient is used for everybody. Such a plate, fixed in terms of height and inclination, therefore leads to a correct mounting of dental prostheses being impossible.

The present invention aims to overcome these disadvantages by providing an articulator making it possible to define a prosthetic orientation plane parametrizable as desired, both in millimeters of height and in degrees of inclination, taking into account the patient's morphology (hyperdivergent, hypodivergent or normodivergent).

To this effect, this articulator, making it possible to parametrize the prosthetic or occlusal orientation plane and the dentoalveolar stages for the purpose of producing dental prostheses, comprises:

two upper and lower planar elements articulated relative to one another about a horizontal axis parallel to the planes of the elements and located above the lower planar element, the two planar elements being intended for fastening two models of a patient's dental arches opposite one another and in contact with one another, specifically an upper model fastened under the lower face of the upper element and a lower model fastened on the upper face of the lower element, means for defining, between the two elements, a plane inclined relative to the upper element and corresponding to an occlusal plane between the two models, said means being carried by the upper element and comprising a plate embodying the occlusal orientation plane.

According to the invention, the means defining the inclined plane comprise means for adjusting the angle of inclination and the distance of the plate in relation to the upper element, and the adjustment of the distance of the plate in relation to the upper element is ensured by means of at least one assembly carried by the upper element and a graduated column carrying at its lower end the plate and sliding perpendicularly to the upper element in the assembly, thus ensuring the guidance of the column and the locking of the latter in a position adjustable relative to the upper element.

The articulator according to the invention makes it possible to manufacture occlusal mock-ups along a prosthetic orientation plane suitable for each patient, this being achieved by means of a double movement about an axis which does not disturb the angular programming selected for the prosthetic orientation plane. The articulator may additionally comprise a compass making it possible to trace the prosthetic orientation plane and the orientation of the line of the gingivodental collars. It also makes it possible to use an anteroposterior sagittal axis allowing the distortion of an occlusal plane, that is to say its asymmetry relative to the base of the skull, to be diagnosed.

The articulator according to the invention makes it possible to obtain a time saving and constant reliability at all the stages of the prosthetic reconstruction work. In its use in orthodontics, by recording the occlusal plane before treatment (coordinates in millimeters of height and degrees of inclination), the orthodontist can, during treatment or after treatment, check the action of the orthodontic appliance in the mouth by once again transferring the spatial situation of the patient's dental arches to the articulator and by carrying out a comparison with initial values (in particular, dentoalveolar compensations).

The articulator according to the invention also makes it possible to diagnose and quantify the asymmetries of the occlusal plane which are responsible inter alia for dental traumatisms having effects on the dental arches and the temporomandibular joints. It also makes it possible to establish a surgical and prosthetic treatment plane before treatment. Stringent parametrization makes it possible to systematize the surgical, orthodontic or prosthetic modifications which a treating doctor considers for his patient.

The appliance is simple and quick to use, which cannot fail to be noticed by practitioners, whatever their field (implant surgery or periodontal, prosthetic or orthodontic surgery), and by prosthesists. Communication regarding the transfer of the patient's models between a dental surgery and a prosthesis laboratory is greatly improved thereby.

Embodiments of the present invention are described below by way of nonlimiting example, with reference to the accompanying drawings in which:

FIG. 2 is a diagrammatic side elevation view of the articulator of FIG. 1, taken from the left of this figure.

FIG. 3 is a diagrammatic elevation view of the articulator, in which the means defining the inclined plane corresponding to the occlusal plane are mounted at the rear of the upper element.

FIG. 4 is a view in vertical section of the skull of a toothless patient whose occlusal plane is incorrect.

FIGS. 5, 6 and 7 are diagrammatic side elevation views illustrating the use of the articulator according to the invention for correcting the upper and lower models of the patient illustrated in FIG. 4 and for obtaining a correct occlusal plane.

FIG. 8 is a view in vertical section of the patient's skull which has resumed a correct occlusal plane.

FIG. 9 is a side elevation view of the graduated column and of an assembly supporting the plate embodying the prosthetic or occlusal orientation plane.

FIG. 10 is an elevation view of the assembly illustrated in FIG. 9, taken from the right of this figure.

FIG. 11 is a view in horizontal section along the line XI—XI of FIG. 9.

FIG. 12 is a side elevation view of the graduated column.

FIG. 13 is a view in horizontal section along the line XIII—XIII of FIG. 12.

FIG. 14 is a side elevation view of the angularly adjustable stop.

FIG. 15 is a plan view of the angularly adjustable stop.

FIG. 16 is a side elevation view of the intermediate connection piece.

FIG. 17 is a plan view of the intermediate connection piece.

FIG. 18 is a partially cutaway elevation view of the pivot axis and of its locking screw.

FIG. 19 is a profile view of the pivot axis, taken from the left in FIG. 18.

FIGS. 20 and 21 are views in vertical section of the assembly supporting the plate, respectively in a position in which the plate is aligned with the angularly adjustable stop and in a position in which the plate is inclined downward in relation to the position of alignment with this adjustable stop.

FIG. 22 is a plan view of an assembly consisting of a slideway, of a graphite-tip compass mountable on the left or on the right, making it possible to trace on the dental arches, and of removable rules capable of being used instead of the plate embodying the prosthetic or occlusal orientation plane.

FIG. 23 is an elevation view of the slideway/rule assembly illustrated in FIG. 22.

FIG. 24 is a profile view of the assembly illustrated in FIG. 22, taken from the left in this figure.

FIG. 25 is a profile view of the assembly illustrated in FIG. 22, taken from the right in this figure.

FIG. 26 is an exploded diagrammatic view of another embodiment of the articulator according to the invention, of which

FIG. 31 is a diagrammatic perspective illustration of the embodiment illustrated in FIGS. 26 and 30 and mounted on the complete articulator.

Figure 1:
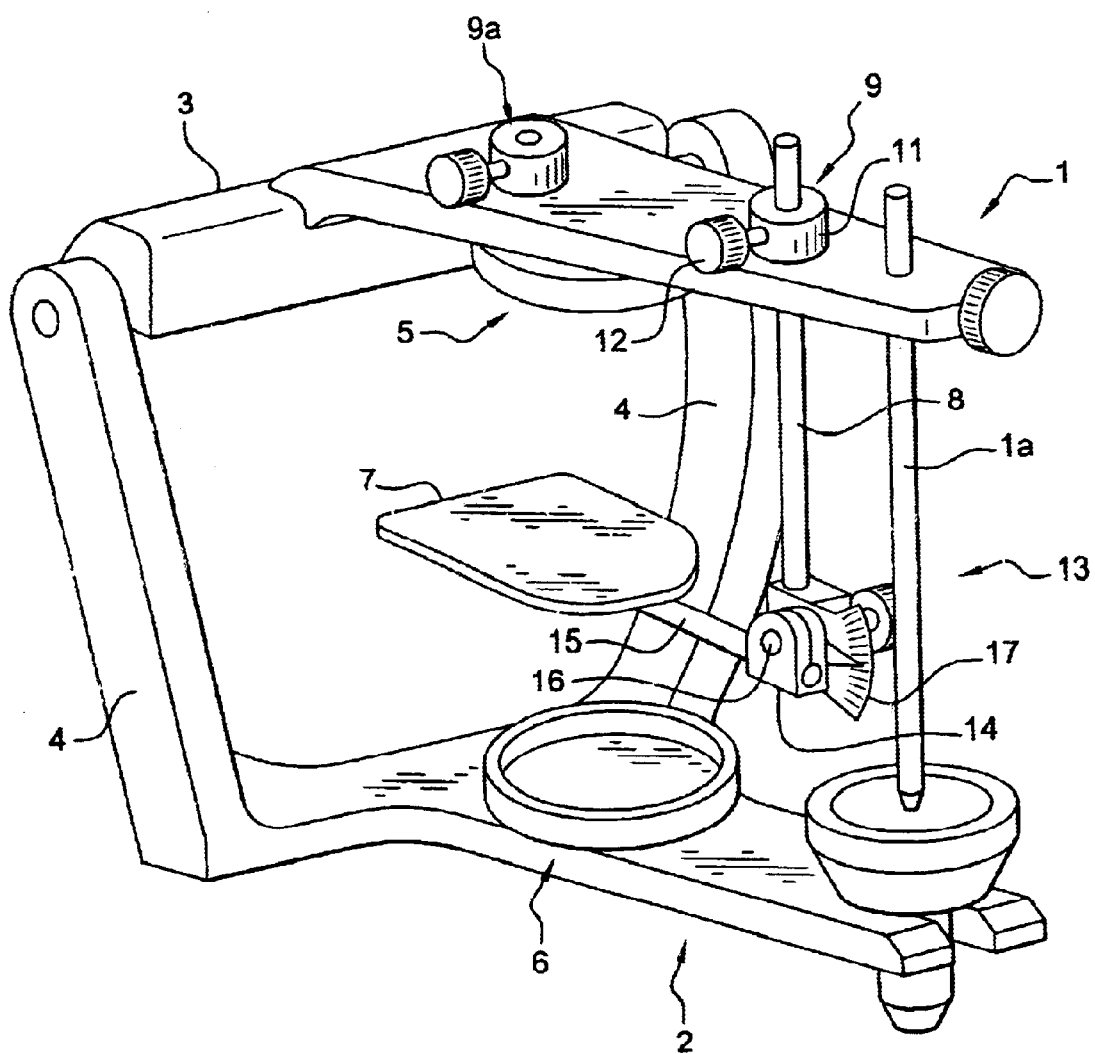
FIG. 1 is a perspective view of an articulator according to the invention, in which the means defining the position of the inclined plane corresponding to the occlusal plane are mounted at the front of the upper element.

The articulator according to the invention, which is illustrated diagrammatically in FIGS. 1 and 2, is of the type of articulators known in the trade by the designation "ARCON". This articulator for producing dental prostheses comprises essentially an upper planar element or member (1) and a lower planar element or member (2), which are articulated relative to one another about a horizontal and transverse axis parallel to the planes of the two elements and located above the lower element (2). The axis (3), corresponding to the bicondylar hinge axis of the articulators, is carried, in fact, by two arms (4) which extend upward from the lower element (2) and which form one piece with the latter. The articulator has a closing position, in which the two elements (1, 2) are substantially parallel to one another. This position is defined by an incisor rod (1a) which passes perpendicularly through the upper element (1) and is locked in an adjustable position and the lower end of which is in contact with a bearing piece mounted on the upper face of the lower element (2), called the incisor plate or table. Said rod makes it possible to preserve the relation between the two dental arches, as it exists in the patient's mouth; this defines a vertical occlusal dimension. This vertical occlusal dimension makes it possible to achieve the esthetic harmony of the lower stage of the face.

The two upper (1) and lower (2) elements respectively embody the upper and lower jaws of a patient for whom a dental prosthesis is to be manufactured. For this purpose, two models of the patient's dental arches are produced in the usual way, specifically an upper model (5) corresponding to the upper dental arch and fastened under the lower face of the upper element (1), and a lower model (6), corresponding to the lower dental arch and fastened on the upper face of the lower element (2). The upper (5) and the lower (6) models, generally produced from plaster, conventionally comprise a respective occlusal mock-up or baseplate (5a) and (6a) made of hard resin and surmounted by respective surface stents (5b), (6b), made of thermoformable material.

Dental prostheses which have to be manufactured, using the articulator according to the invention, must be established from upper (5) and lower (6) models which, when the articulator is closed (the position illustrated in FIGS. 1 and 7) are in contact along an occlusal plane p which is inclined from the rear forward and from the top downward at an angle α, the value of which is equal to or in the vicinity of 10° in a normodivergent patient. For this purpose, the articulator according to the invention is provided with means which make it possible to predetermine the position of this occlusal or prosthetic orientation plane in millimeters of height and in degrees of inclination in relation to a reference consisting of the abovementioned Frankfurt plane.

According to the invention, the means defining the inclination plane corresponding to the desired occlusal orientation plane P are carried by the upper element (1) of the articulator and comprise a thin plate (7), intended for embodying the prosthetic or occlusal orientation plane, and means for adjusting the angle of inclination and the distance of the plate (7) in relation to the upper element (1). These adjustment means comprise a graduated column (8) sliding perpendicularly relative to the plane of the upper element (1) in at least one guiding and locking assembly (9). In the nonlimiting embodiment illustrated in the figures, in fact, the articulator comprises two guiding and locking assemblies, specifically an anterior assembly (9) and a posterior assembly (9a), the posterior assembly (9a) being mounted on the upper element (1) in a position nearer to the horizontal axis of articulation (3) than the anterior assembly (9). Each guiding and locking assembly (9, 9a) may comprise a sleeve (11), through which the graduated column (8) passes completely and which is arranged coaxially relative to a through orifice made underneath in the upper element (1). The column (8) is locked in any desired vertical position by means of a screw (12) which is screwed into a threaded radial hole of the sleeve (11) and the end of which comes to bear on the graduated column (8) within the sleeve (9). The graduated column (8) is guided in the sleeve (9), without being capable of rotating about its axis, and, for this purpose, said column may have a noncircular, for example square cross section.

The graduated column (8) carries, at its lower end, an assembly (13) supporting the plate (7) and making it possible to vary the degree of inclination of the latter. A nonlimiting embodiment of this assembly (13) will be described later with reference to FIGS. 9 to 21. The assembly (13) comprises, in the example of FIG. 1, a tubular support (14) in which a rod (15) integral with the plate (7) is engaged. The tubular support (14) is articulated on the lower end part of the graduated column (8) about a horizontal axis (16) which is parallel to the axis of articulation (3) between the two elements (1) and (2). The degree of inclination α of the tubular support (14) and consequently of the plate (7) about the pivot axis (16) in relation to the plane of the upper element (1) is indicated by means of a vernier (17) integral with the lower end part of the graduated column (8).

As an example of the use of the articulator according to the invention, its use will now be described for correcting an incorrect occlusal plane P, as illustrated in FIG. 4, and for obtaining a correct occlusal plane P, as illustrated in FIG. 8. At the outset, the incorrect occlusal plane P, which occurs as result of the complete toothlessness of a patient (FIG. 4), is inclined from the bottom upward and from the rear forward, that is to say in the opposite direction to the correct inclination. In order to correct this defect, for the sake of convenience for the prosthesist the appliance is used with the adjustment means located in the rear position, that is to say with the graduated column (8) engaged in the posterior guiding and locking assembly (9a), as may be seen in FIG. 3. The upper (5) and lower (6) models fastened respectively to the elements (1) and (2), as illustrated in FIG. 3, correspond to those taken on the patient, and they reproduce the incorrect inclination of the occlusal plane P. The prosthesist can then parametrize the use of the appliance, that is to say determine in advance the height of the plate (7) and its inclination for the purpose of the future reconstruction. The prosthesist therefore locks the graduated column (8) at the desired height in the assembly (9a), and, after having softened the stent of thermoformable material (5b) of the upper model (5) by heating and having opened the articulator, he taps with the plate (7) on the softened stent (5b), at the same time causing this plate (7) to oscillate about the pivot axis (16), as indicated by the arrow f in FIG. 3, until the softened stent (5b) is induced to have a planar lower face located at the intended height and inclined at the desired angle α for the occlusal plane P. The final situation resulting from the tapping of the stent (5b) by the plate (7) is illustrated in FIG. 5. During this operation of modeling the stent (5b) of the upper model (5), the lower model (6) is held in place on the lower element (2), still set apart from the upper element (1). After the cooling and curing of the upper stent (5b) with a planar lower surface, the plate (7) is removed from its support (14) (FIG. 6), the thermoformable stent (6b) of the lower model (6) is heated so as to soften it, and the articulator is closed to the vertical dimension recorded in the mouth and defined by the height of the incisor rod (1a). As a result of the pressure exerted, the softened lower stent (6b) is deformed on contact with the cured upper stent (5b), and the lower stent (6b) then assumes a planar upper face which is adjacent to the lower face of the upper stent (5b). These two faces are then contained in the occlusal plane p which is located at the intended height and is inclined at the desired angle α for this plane. FIG. 8 illustrates the two upper and lower models having a correct occlusal plane P and placed in the mouth.

In the generality of uses of the articulator, the plate (7), intended for defining the position of the occlusal plane P, has only a single degree of freedom, that is to say it can simply pivot about the horizontal axis of articulation (16). However, it may also be envisaged to give the plate (7) an additional degree of freedom by allowing it to pivot transversely toward the left and toward the right about the axis of its supporting rod (15).

There will now be described, with reference to FIGS. 9 to 21, a nonlimiting embodiment of the assembly (13), as mounted alternatively in FIGS. 3 and 5 to 7, supporting the plate (7) and making it possible to vary its degree of inclination a relative to the horizontal and to the upper element (1) of the articulator. This assembly (13) comprises, first of all, a fork (18) which is formed at the lower end of the graduated column (8) and which extends toward the right, as may be seen more clearly from FIGS. 12 and 13. The graduated column (8), seen in elevation, thus has an L-shape. The two parallel branches of the fork (18) are pierced respectively with coaxial holes (19) intended for receiving and supporting the pivot axis (16) of the assembly (13).

The assembly (13) comprises, furthermore, two pieces fitted one into the other and articulated jointly about the pivot axis (16), specifically an angularly adjustable stop (21), illustrated in detail in FIGS. 14 and 15, and an intermediate connection piece (22), illustrated in detail in FIGS. 16 and 17.

The adjustable stop (21), which is laid against a vertical lateral face of the lower part of the column (8) or of the lower fork (18) of the column (8), comprises, in its right part, a through orifice (23) of the same diameter as that of the pivot axis (16) and intended for receiving this axis, and, in its outer face, a blind hole (24) arranged between the orifice (23) and the right vertical side (25) of the adjustable stop (21). In its left part, the stop (21) has an oblong slot (26) in the form of an arc of a circle centered on the center of the orifice (23), and one edge of said slot carrying a graduation (27). This curved slot (26) extends opposite a threaded blind hole (28) made within the vertical lateral face of the column (8) or of the fork (18) against which the adjustable stop (21) is laid. When this adjustable stop is in the horizontal position or "zero" position, the threaded hole (28) is aligned horizontally with the orifices (19) provided for receiving the axis (16). A locking screw (29) is screwed into the blind hole (28), at the same time passing through the arcuate slot (26), and is intended for ensuring that the adjustable stop (21) is locked in any desired angular position relative to the horizontal, after said stop has been pivoted about the axis (16).

It goes without saying that the upper graduated part of the stop (21), which part is located on the right in FIGS. 9, 14, 20 and 21 and is symmetrical to the lower graduated part with respect to the horizontal, is used in the same way when the column (8) supporting the assembly (13) is mounted at the front of the articulator, that is to say in the guiding and locking assembly (9), as illustrated in FIGS. 1 and 2.

The intermediate connection piece (22) is itself mounted pivotably about the axis of articulation (16). It is coupled to the plate (7) by means of a fork (31), that is to say U-shaped, which is fastened with its transverse web to the rear or left transverse side (7a) of this plate (7) and the parallel wings of which extend rearward, that is to say toward the pivot axis (16). This fork (31), which is illustrated more clearly in FIGS. 22 and 24, has, on the inner faces of its web and of its wings, a continuous groove (31a), in which engages a rib (32) of complementary shape, formed on the outside of the intermediate connection piece (22). This intermediate piece (32) has, moreover, two coaxial holes (33) through which the pivot axis (16) passes, in order to allow the intermediate connection piece (22) to pivot about this axis (16). The pivoting movement of the intermediate connection piece (22) and consequently of the plate (7) can take place freely only downward, the upward pivoting stroke of the piece (22) being limited by its encountering the right vertical side (25) of the adjustable stop (21). In other words, the intermediate piece (22) and the plate (27) can pivot freely upward only as far as an upper end position in which the plate (7) is aligned with the adjustable stop (21), as illustrated in FIG. 20. FIG. 21 illustrates the possibility for the downward pivoting F of the intermediate piece (22) and of the plate (7) in relation to the stop (21).

The piece (22) may, however, be locked on the adjustable stop (21) when the plate (7) is to be held in the desired inclined position determined by the inclination of the adjustable stop (21). This locking is carried out by means of a screw (34) which passes through a smooth orifice made within a wing of the fork (31) and which cooperates with a threaded hole (35) (FIG. 17) made in the intermediate connection piece (22), so as to engage with its end into the blind hole (24) formed in the adjustable stop (21).

FIGS. 18 and 19 illustrate the pivot axis (16) which terminates at one end in a rectangular collar (36) and which, in the region of its opposite end part, has a threaded axial hole, into which is screwed a screw (37) for locking the axis (16) in position.

It may be gathered from the foregoing description that the position of the prosthetic or occlusal orientation plane can be determined in advance by the practitioner, by locking the adjustable stop (21) in the desired angular position about the axis (16) by means of the screw (29), this stop then determining the end of the upward pivoting stroke of the intermediate connection piece (22) and of the plate (7). This makes it possible, without canceling the programming of the locking of the adjustable stop (21) on the graduated column (8), to cause the plate (7) to tilt downward and to return it upward according to the double arrow F of FIG. 21, as far as the upper position in which it is detained by the stop (21).

With reference to FIGS. 22 to 25, an alternative embodiment is now described, which can be used when the dental prosthesis to be produced is for a partially toothed patient. It may happen, in fact, that a patient has, on one side, correctly situated dental stages, whereas, on the other side, there is not the same situation, for example as result of an extraction (all the bottom teeth having been extracted and the top teeth having descended, etc.). This results in confusion as regards the level given to the future occlusal plane. In such a case, the practitioner uses, instead of the continuous plate (7) described above, a "partial plate" which, in fact, consists of a rule mounted on a slideway forming a support (41), said slideway itself being integral, in the region of its rear face, with the fork (31) coupled to the intermediate connection piece (22) of the articulated assembly (13), and said slideway carrying one or more interchangeable rules (42–45) on its front face.

FIG. 22 illustrates by way of example four rules of different shapes (42, 43, 44, 45) which comprise respectively planar horizontal parts of small width, L-shaped (42), trapezoidal (43, 45) or else in the form of a right-angled triangle (44). Each of the rules (42–45) is coupled to the slideway (41) by any assembly means, for example of the dovetail type. By means of the suitable rule (42–45) inserted between the top teeth and bottom teeth of the healthy side, the practitioner can record the joining level of these teeth, that is to say the occlusal orientation plane, on the healthy side. The L-shaped rule (42) can come into place in the middle zone in order, where appropriate, to ascertain in the frontal plane an inclination to the left or to the right and misalignment in the vertical direction of the incisors or canines. The rule (43) can be used for a lateral sector, since it can be placed exactly parallel on the healthy lateral side. On the side where there is an absence of teeth, one of the rules can be inserted between two maxillaries.

Associated with the partial plate, illustrated in FIG. 22 and consisting of the slideway (41) and one of the rules (42–45), is a compass (46), one (47) of the branches of which is articulated about an axis (48) perpendicular to the plane of the rules (42–45) at one or other of the ends of the rule (41). The other branch (49) of the compass (46) is articulated on the first branch (47) about an axis (51). The branch (49) carries at its free end a tracing element (52) comprising, for example, a graphite tracing tip (53) which extends parallel to the plane of the rules (42–45). It is therefore possible, using the compass (46), to trace, on the existing teeth in place which have dropped, the height level which it is appropriate to restore to them. The tracing tip (53) is always displaced in the programming plane, that is to say in the desired prosthetic or occlusal orientation plane.

Another embodiment of the invention has been illustrated in connection with FIGS. 26 to 31. The operating principle, of course, remains the same as that described above. The vertical slide or column (8), having a cross section other than circular, so as to prevent any pivoting in the vertical direction, has, at its base, a widened portion (60) intended for cooperating with a reading index (55) described in more detail below. This vertical slide (8) receives, on its outer face, a rigid insert (75) carrying graduations in millimeters and in degrees, which is illustrated more clearly in FIG. 29. This insert, for example made of cardboard, comprises, in fact, a vertical millimeter scale, intended to make it possible to fasten the plate (7) at the desired height, and a scale in degrees of angle, intended to make it possible to orient said plate likewise according to the desired angulation. This insert is received in a T-shaped groove (not illustrated), thus making it possible to fasten it in the region of the slide (8).

Said base (60) of the vertical slide (8) comprises, furthermore, two vertically aligned orifices (61, 62):
- one (61), blind and provided with a thread and intended for receiving a screw (63) for locking the desired angulation of the plate (7), as described below;
- the other (62), a through hole, intended for receiving a pivot axis (64), making it possible to modify the angulation of said plate in relation to the base (60) of the slide (8).

Figure 26:
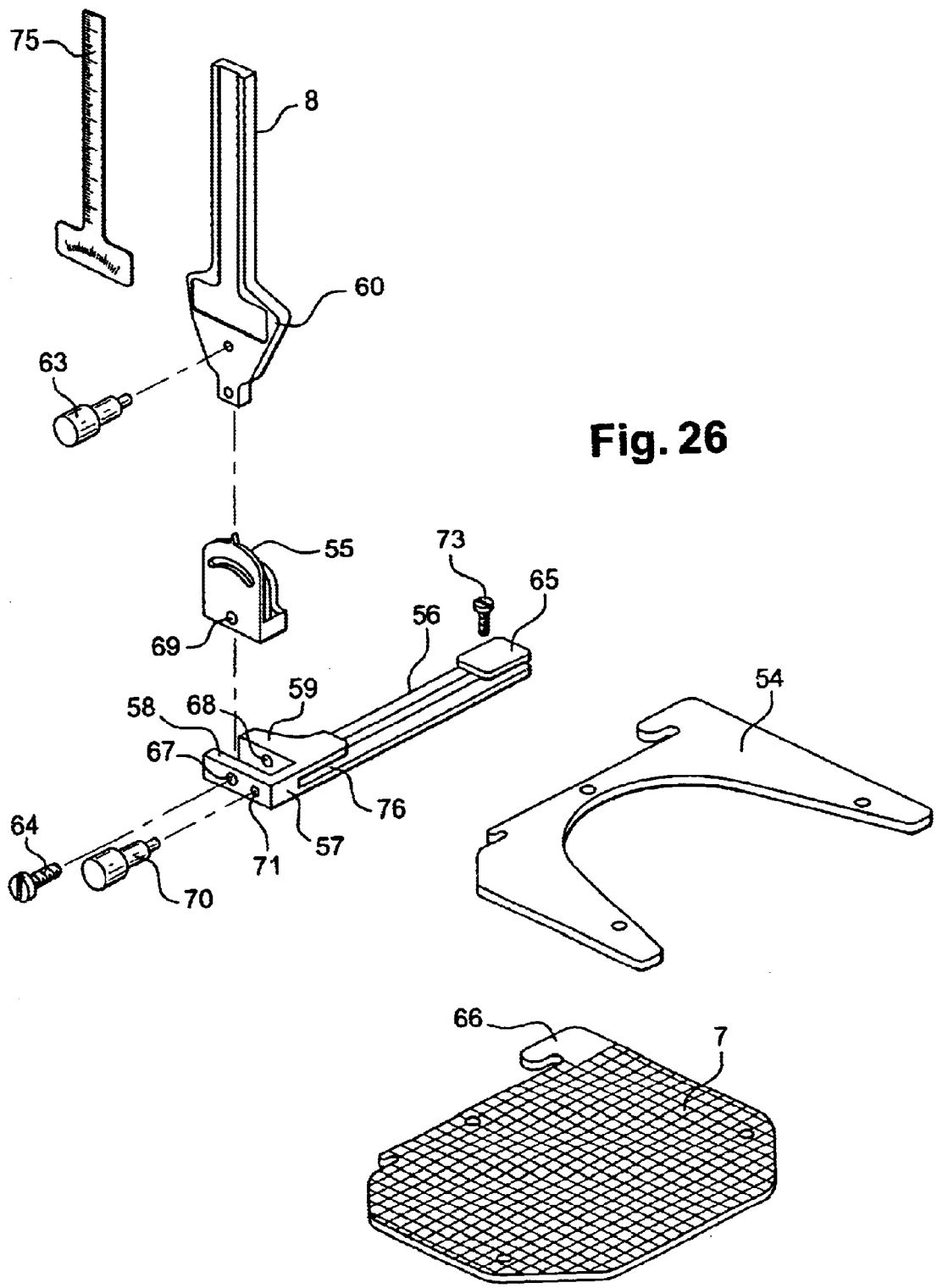
Figure 27:
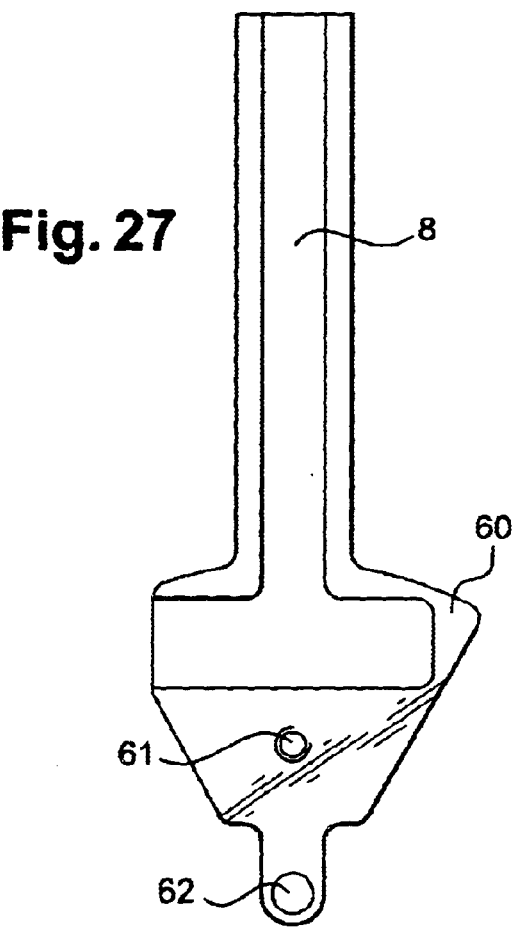
FIG. 27 is a detailed view of the vertical slide, FIG. 28 a diagrammatic view of the index for reading the graduations and FIG. 29 a view of the graduations affixed to a pad to be fastened to said slide.

As may be seen in FIG. 26, the base (60) cooperates with the plate (7) by means of an intermediate connection piece (56) oriented horizontally and perpendicularly relative to said vertical slide (8). As may be seen in this figure, said plate (7) is removable and is inserted into said piece (56) in the region of a groove (76) and of a catch (65) intended for cooperating with a slot (66) made in the region of the base of said plate. Moreover, this groove is likewise capable of receiving a yoke (54), the function of which will be described in more detail later. The system, as described, for assembling the accessories (plate, yoke) in the region of the intermediate piece has been described by way of nonlimiting example. The plate (7) and the yoke (54) are held engaged in the groove (76) of the intermediate piece by friction. It is conceivable to use a screw (73) in the region of the catch (65), thus assisting this immobilization.

This intermediate connection piece (56) has, in the region of one of its ends, a fastening zone (57) provided with two branches (58, 59) intended to be slipped on either side of the lower end of the base (60) of the vertical slide (8). More specifically, in addition to said base (60), the graduation reading index (55) is likewise inserted between the branches (58, 59). Thus, the abovementioned pivot axis (64) is inserted into a through orifice (67), then into a through orifice (69) made at the lower end of the index (55) and then into an orifice provided with a thread (68) and made in the branch (59) of the end (57) of the piece (56).

Moreover, the index (55) is locked in position within the end (57) of the intermediate piece (56) by means of a screw (70) passing through an orifice (71) and made in the branch (58) and coming to bear on the face of said index.

Figure 28:
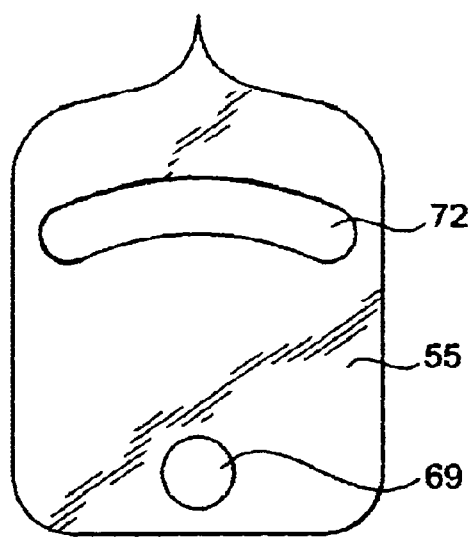
Figure 29:
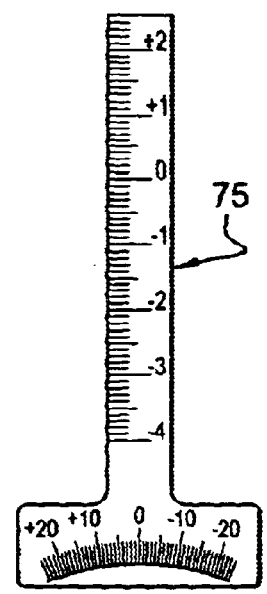
Figure 30:
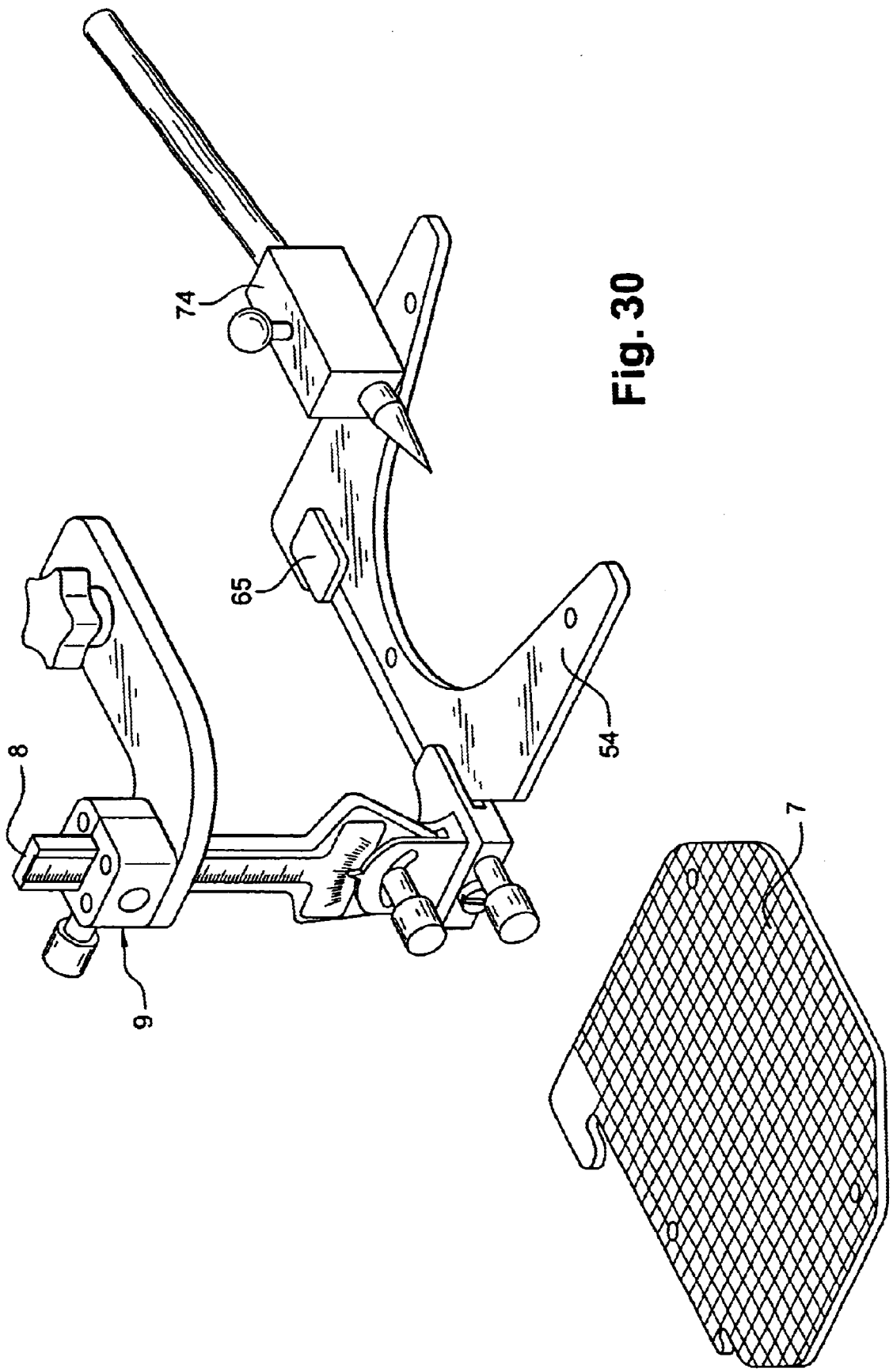
FIG. 30 is a partially exploded diagrammatic view of the embodiment illustrated in FIG. 26.

As can be seen more clearly in FIG. 28, the index (55) has an arcuate window (72) intended to come opposite that zone of the graduation (75) which is graduated in degrees, when the assembly is in place.

The abovementioned yoke (54) is intended to make it possible to check the respective levels of the right, anterior and left alveolodental structures and, by means of a tracing member (74) (see FIG. 30) led flat on the upper surface of said yoke, to trace a strictly angulated trace, to the required millimeter accuracy, on the models of the patient's arches.

The example of the use of the articulator according to the invention, as described above, is only one of the possibilities for using this articulator. In particular, it may be employed to correct an absence of molars at the back of the jaws, or even a crushing of the lower stage, by occlusal mock-ups being manufactured, which take the place of the missing molars. Another possible use is to manufacture occlusal models to compensate for the absence of teeth on only one side. Other uses will obviously be gathered by persons skilled in the art.

What is claimed is:

1. An articulator for parametrizing a prosthetic or occlusal orientation plane and dentoalveolar stages for producing dental prostheses, said articulator comprising an upper planar element and a lower planar element articulated relative to one another about a horizontal axis of articulation (3) parallel to the planes of the elements (1, 2) and located above the lower planar element (2), the upper planar element and the lower planar element configured to simultaneously fasten an upper model of a patient's dental arches under a lower face of the upper element (I) and a lower model (6) of the patient's dental arches on an upper face of the lower element (2), and means for defining, between the upper element and the lower element (1, 2), a plane inclined relative to the upper element (1) and corresponding to an occlusal plane P between the upper model and the lower model, said means for defining corresponding to the occlusal plane P being carried by the upper element (I) and comprising a plate (7) embodying the occlusal orientation plane P; and wherein the means for defining the occlusal orientation plane P comprise means (8, 9; 13; 56–59; 65–70) for adjusting the angle of inclination and the distance of the plate (7) in relation to the upper element (1) when the upper model is fastened to the upper element and the lower model is fastened to the lower element; and wherein the adjustment of the distance of the plate (7) in relation to the upper element (1) is performed by at least one first assembly (9) connected to the upper element (1) and a column, said column (8) having graduation (8) and being connected at its lower end to the plate (7) and sliding perpendicularly to the upper element (1) in the first assembly (9) to guide the column (8) and to lock the column in a position adjustable relative to the upper element (1) and wherein the adjustment of the angle of inclination of the plate (7) in relation to the upper element (1) is performed by the at least one first assembly (9) connected to the upper element (1) and the column (8), said column (8) carrying at its lower end, a second assembly (13) which carries the plate (7) pivotable about an axis (16) parallel to the axis of articulation (3) between the upper planar element and the lower Planar element.

2. The articulator as claimed in claim 1, characterized in that the upper element (1) comprises two anterior (9) and posterior (9a) guiding and locking assemblies, the posterior guiding and locking assembly (9a) being nearer to the axis of articulation (3) of the two elements (1, 2) than the anterior assembly (9).

3. The articulator as claimed in claim 2, characterized in that the column (8) carries, in its lower part, an assembly (13) which carries the plate (7) pivoting about an axis (16) parallel to the axis of articulation (3) between the two elements (1, 2) of the articulator.

4. The articulator as claimed in claim 3, aracterized in that the assembly (13) comprises:

an adjustable stop (21) mounted rotatably about the pivot axis (16) of the plate (7);

means (26, 28, 29) for locking the adjustable stop (21) in the angular position relative to the upper element (1), corresponding to the desired inclination of the prosthetic or occlusal orientation plane, an intermediate connection piece (22) which is integral with the plate (7), is fitted on the adjustable stop (21)

and is mounted rotatably about the pivot axis (16) and the upward pivoting stroke of which is detained by the stop (21);

and means (34) for locking the intermediate connection piece (22) on the adjustable stop (21).

5. The articulator as claimed in claim 3, characterized in that the column (8) has, in its lower part, a fork (18), the two parallel branches of which are pierced with coaxial holes (19) supporting the pivot axis (16) of the plate (7).

6. The articulator as claimed in claim 1, characterized in that the assembly (13) comprises:

an adjustable stop (21) mounted rotatably about the pivot axis (16) of the plate (7); means (26, 28, 29) for locking the adjustable stop (21) in the angular position relative to the upper element (1), corresponding to the desired inclination of the prosthetic or occlusal orientation plane, an intermediate connection piece (22) which is integral with the plate (7), is fitted on the adjustable stop (21) and is mounted rotatably about the pivot axis (16) and the upward pivoting stroke of which is detained by the stop (21);

and means (34) for locking the intermediate connection piece (22) on the adjustable stop (21).

7. The articulator as claimed in claim 6, racterized:

in that the adjustable stop (21) is laid against a vertical lateral face of the lower part of the column (8), in that said stop (21) comprises a through orifice (23) of the same diameter as that of the pivot axis (16) and intended for receiving this axis, in that the stop (21) comprises, in its outer face, a blind hole (24) arranged between the through orifice (23) and a vertical side (25) of the adjustable stop (21), in that the stop (21) has, on the other side of the through orifice (23), an oblong slot (26) which is in the form of an arc of a circle centered on the center of the through orifice (23) and one of the edges of which carries a graduation (27), this oblong slot (26) extending opposite a threaded blind hole (28) which is made in the vertical lateral face of the column (8), against which the adjustable stop (21) is laid, and is intended for cooperating with a locking screw (29) inserted through the oblong slot (26), thus making it possible to lock the adjustable stop (21) in any desired angular position in relation to the upper element (1).

8. The articulator as claimed in claim 6 characterized in that the intermediate connection piece (22) is coupled to the plate (7) by means of a fork (3 1) of suitable shape, which is fastened with its transverse web to the rear transverse side (7a) of said plate (7) and the parallel wings of which extend rearward in the direction of the pivot axis (16).

9. The articulator as claimed in claim 8, characterized in that it comprises a screw (34) passing through a hole pierced in a wing of the fork (31), and a threaded hole (35) made within the intermediate connection piece (22), so as to engage with its end into the blind hole (24) formed in the adjustable stop (21), in order to lock the plate (7) in the desired inclined position on the adjustable stop (21).

10. The articulator as claimed in claim 8, characterized in that it comprises a partial plate consisting of a slideway (41) which is integral on its rear face with the fork (31) coupled to the intermediate connection piece (22) of the assembly (13) and which carries on its front face one of a plurality of interchangeable rules (42–45).

11. The articulator as claimed in claim 10, characterized in that each rule (42–45) comprises a planar horizontal part of small width, L-shaped, trapezoidal or in the form of a right-angled triangle, and a means of assembly with the slideway (41).

12. The articulator as claimed in claim 10, characterized in that it comprises a compass (46), one (47) of the branches of which is articulated about an axis (48) perpendicular to the plane of the rules (42–45) at one or other of the ends of the slideway (41), and the other branch (49) of which is articulated on the first branch (47) about an axis (51) and at its free end carries a tracing element,(52) extending parallel to the plane of the rules (42[]45).

13. The articulator as claimed in claim 6, characterized in that the column (8) has, in its lower part, a fork (18), the two parallel branches of which are pierced with coaxial holes (19) supporting the pivot axis (16) of the plate (7).

14. The articulator as claimed in claim 1, characterized in that the column(8) has, in its lower part, a fork (18), the two parallel branches of which are pierced with coaxial holes (19) supporting the pivot axis (16) of the plate (7).

15. The articulator as claimed in claim 1, characterized in that the column (8) has, on its outer face, a T-shaped groove intended for receiving a rigid insert (75) carrying the graduations in millimeters and in degrees.

16. The articulator as claimed in claim 1, characterized in that the column (8) has, in its lower part, a base (60) intended for cooperating with an intermediate connection piece (56) carrying the plate (7) removably and capable of making it possible to give said plate the desired inclination.

17. The articulator as claimed in claim 16, characterized in that the intermediate connection piece (56) has, in the region of one of its ends, a fastening zone (57) provided with two branches (58, 59) intended to be slipped on either side of the lower end of the base (6) of the column (8).

18. The articulator as claimed in claim 17, characterized in that, in addition to the base (6) of the column (8), a graduation reading index (55) is inserted between the branches (58, 59) of the fastening zone (57).

19. The articulator as claimed in claim 16, characterized in that it comprises, furthermore, a yoke (54) capable of coming into position in the region of the intermediate connection piece (56) and intended to make it possible to check the respective levels of the right, anterior and left alveolodental structures and, by means of a tracing member (74) associated with it and led flat on the upper surface of said yoke, to trace a strictly angulated trace on the models of the patient's arches.

20. An articulator for parametrizing a prosthetic or occlusal orientation plane and dentoalveolar stages for producing dental prostheses, said articulator comprising:

an upper planar element attachable to an upper dental arch model;

a lower planar element attachable to a lower dental arch model, said upper planar element and said lower planar element being articulated relative to one another about a horizontal axis of articulation parallel to the planes of the elements and located above said lower planar element;

said upper planar element being attachable to the upper dental arch model simultaneous to said lower planar element being attachable to the lower dental arch model;

a plate for embodying an occlusal plane between the upper arch model and the lower arch model, said plate operatively mounted to said upper planar element;

said plate being adjustable in angle of inclination and distance of said plate relative to said upper element;

at least one first assembly connected to the upper planar element and a column;

said column configured to slide perpendicularly relative to the upper planar element in the first assembly to guide the column and configured to lock the column in a position relative to the upper planar element; and said column carrying, at its lower end, a second assembly which carries the plate pivoting about an axis parallel to the axis of articulation between the upper planar element and the lower planar element.

21. The articulator of claim 20 wherein said plate is adjustable when said upper arch model is attached to said upper planar element and said lower arch model is attached to said lower planar element.

* * * * *

UNITED STATES PATENT AND TRADEMARK OFFICE
CERTIFICATE OF CORRECTION

PATENT NO. : 6,616,449 B1
DATED : September 9, 2003
INVENTOR(S) : Rocher

It is certified that error appears in the above-identified patent and that said Letters Patent is hereby corrected as shown below:

Column 10,
Line 34, delete "(8)" after the word "graduation"
Line 58, delete the word "aracterized" and insert -- characterized --

Column 11,
Line 23, delete the word "racterized" and insert -- characterized --
Line 46, delete "(3 1)" and insert -- (31) --

Column 12,
Line 8, delete "(42[]45)" and insert -- (42-45) --

Signed and Sealed this

Sixteenth Day of December, 2003

JAMES E. ROGAN
*Director of the United States Patent and Trademark Office*